(12) United States Patent
Pirli

(10) Patent No.: US 10,478,358 B2
(45) Date of Patent: Nov. 19, 2019

(54) PHYSICALLY DISABLED PATIENT SUPPORT UNIT

(71) Applicant: Aslan Ali Pirli, Gebze (TR)

(72) Inventor: Aslan Ali Pirli, Gebze (TR)

(*) Notice: Subject to any disclaimer, the term of this patent is extended or adjusted under 35 U.S.C. 154(b) by 364 days.

(21) Appl. No.: 15/116,714

(22) PCT Filed: Feb. 4, 2015

(86) PCT No.: PCT/TR2015/000039
§ 371 (c)(1),
(2) Date: Aug. 4, 2016

(87) PCT Pub. No.: WO2015/119586
PCT Pub. Date: Aug. 13, 2015

(65) Prior Publication Data
US 2016/0346145 A1 Dec. 1, 2016

(30) Foreign Application Priority Data
Feb. 6, 2014 (TR) .................................. 2014/01377

(51) Int. Cl.
*A61G 7/02* (2006.01)
*A61F 5/451* (2006.01)
(Continued)

(52) U.S. Cl.
CPC ................ *A61G 7/02* (2013.01); *A61F 5/442* (2013.01); *A61F 5/451* (2013.01); *A61F 5/453* (2013.01);
(Continued)

(58) Field of Classification Search
CPC ........ A61G 7/02; A61G 7/0509; A61G 7/005; A61G 7/012; A61G 7/015; A61G 7/018;
(Continued)

(56) References Cited

U.S. PATENT DOCUMENTS 3,933,636 A * 1/1976 Daniels .................. B60R 15/04
210/739
4,821,348 A * 4/1989 Pauna .................. A61G 7/0005
4/547

(Continued)

FOREIGN PATENT DOCUMENTS

| JP | H1085275 A | 4/1998 |
| WO | 2008041959 A2 | 4/2008 |

(Continued)

OTHER PUBLICATIONS

International Search Report, Application No. PCT/TR2015/000039, dated Jul. 3, 2015, 4 pages.

*Primary Examiner* — Nicholas F Polito
*Assistant Examiner* — Rahib T Zaman
(74) *Attorney, Agent, or Firm* — Ziegler IP Law Group, LLC

(57) ABSTRACT

A physically disabled patient support unit includes functional underwear, a silicone casing shell, tapered duct, ring, slide, inclined waste pump, waste storage, moving step, waste transfer station, safety belt with apparatus and multistage apparatus parts. The support unit provides for the transfer of urine and fecal waste of bedridden physically disabled patients to sewerage without touching. The support also has a very simple and practical use due to its various positions.

8 Claims, 19 Drawing Sheets

(51) Int. Cl.
*A61F 5/453* (2006.01)
*A61F 5/455* (2006.01)
*A61G 5/00* (2006.01)
*A61G 5/10* (2006.01)
*A61F 5/442* (2006.01)
*A61G 7/005* (2006.01)
*A61G 7/012* (2006.01)
*A61G 7/015* (2006.01)
*A61G 7/018* (2006.01)
*A61G 7/05* (2006.01)
*A61G 7/057* (2006.01)

(52) U.S. Cl.
CPC .............. *A61F 5/455* (2013.01); *A61G 5/006* (2013.01); *A61G 5/1002* (2013.01); *A61G 7/005* (2013.01); *A61G 7/012* (2013.01); *A61G 7/015* (2013.01); *A61G 7/018* (2013.01); *A61G 7/0507* (2013.01); *A61G 7/0509* (2016.11); *A61G 7/0573* (2013.01)

(58) Field of Classification Search
CPC .... A61G 7/0507; A61G 7/0573; A61G 7/047; A61G 5/006; A61G 5/1002; A61F 5/442; A61F 5/451; A61F 5/453; A61F 5/455
See application file for complete search history.

(56) References Cited

U.S. PATENT DOCUMENTS

| | | | | |
|---|---|---|---|---|
| 5,058,222 | A | * 10/1991 | Workman | A61G 5/04 4/453 |
| 5,269,030 | A | * 12/1993 | Pahno | A61G 7/0005 4/480 |
| 7,562,400 | B2 | * 7/2009 | Graham | A47K 11/04 4/480 |
| 8,490,224 | B2 | * 7/2013 | Al-Jafar | A61G 5/125 4/480 |
| 2012/0150081 | A1 | * 6/2012 | Pirli | A61F 5/451 601/49 |

FOREIGN PATENT DOCUMENTS

WO    WO2008041959 A2 *  4/2008
WO       2010098731 A2     9/2010

* cited by examiner

PHYSICALLY DISABLED PATIENT SUPPORT UNIT

The aspects of the disclosed embodiments are related to the development of the patent application of physically disabled patient support unit registered with application number TR-2009/01453.

The aspects of the disclosed embodiments include a functional underwear, silicone casing shell, tapered duct, ring, slide, inclined waste pump, waste storage, moving step, waste transfer station, safety belt with apparatus and multi-stage apparatus parts. The invention provides the transfer of urine and fecal waste of bedridden physically disabled patients to sewerage without touching. The invention also has a very simple and practical use due to its various positions.

THE DETAILED EXPLANATION OF THE INVENTION

Functional Underpants Equipment (1) Functional Underwear Device (1)

It covers all the technical properties of the Physically Handicapped Patient Support Unit as specified in the patent application no. TR-2009/01453. New features have been added to provide more efficient use of these properties by the patient and to improve patient comfort. The functional underwear device (1) is placed inside the underwear designed as a corset and fixed to the patient by centering the patient's anus after separating the buttocks to both sides. There are pallets (43) which collaterally support both calves of the patient connected to functional underwear device (1) from below, support the fixation of the underwear on the patient and can move independently. The surfaces of these pallets and the surface of the functional underwear device (1) in contact with the butt of the patient are coated with a material such as antiperspirant, anti-bacterial, soft viscose sponge or air-inflatable pad. These materials are furnished with properties and thickness suitable for the silicone shell casing (2) upper portion end part (3) level and the physical form and weight of the patient and fixed to the patient. On the functional underwear device (1) fixed to the patient, distance between the upper portion end part (3) of the silicone shell casing (2) and the area in contact with the area around the anus will be 4-5 mm. That is, the upper portion end part (3) of the silicone shell casing (2) will contact the patient's body only when the motion sensors detect the discharge of waste from the patient and fully automatically activates the necessary mechanisms. With the support of the electromagnetic coil (18) located inside the rail mechanism (19) fixed on the lower portion of the functional underwear device (1), the inclined waste pump (13) is raised by 4-5 mm, and the upper portion end part (3) of the silicone shell casing (2) contacts the area around the anus and prevents the leakage of odor and stool. At the same time, the slide (10) is opened rapidly by the electromagnetic coils (18), and the waste flows into the pump (13) in a controlled manner, and other operations are performed in turn.

There is a chassis (15) in the functional underwear device (1) located between the two legs of the patient. A mechanism (16) is mounted on this chassis. The mechanism (16) supports the adjustment of the urine removal apparatus (17) designed separately for men and women to the desired level. In addition, in order to be able to adjust the urine removal apparatus to different sizes, the chassis (15) is provided with a movable mechanism (11) support and position adjustment freedom thanks to the holes on the mechanism (16) and the multiple holes on the urine removal apparatus (17). The urine removal apparatus is equipped with a motion sensor (44) and an urine area ejector (45) to clean the urine area with hygienic material. The urine removal apparatus (17) is designed to meet the need for hygienic cleaning and is made of soft silicone.

The urine removal apparatus (17) for women is designed to be in contact with the outer surface of the uterus to prevent the urine from leaking out around the patient's body. It removes urine safely and transfers the waste to the outlet of the pump (13) and transfers it to the waste storage.

Silicone Shell Casing (2)

The silicone shell casing (2) is made of a material such as soft silicone etc. designed to contact the upper surface of the functional underwear device (1) on the one end and to fit to the ergonomics of the upper surface cap of the functional underwear device (1) on the lower edge. In addition, the upper portion end part (3) end of the silicone shell casing (2) contacting the anus is extremely thin towards the end and it is provided with flexibility to prevent any discomfort to the patient. It is designed as a shell to prevent the leakage of the waste to the interior part containing functional underwear device (1) equipment in case the waste of the patient flows over the upper portion end part (3) due to any failure (slide (10) not opening etc.).

Tapered Duct (4)

The upper portion of the tapered duct (4) mounted inside the functional underwear device (1) is hidden inside the silicone shell casing (2) and its lower portion is fixed to the top cover of the slide (10) with the ring (6). The two sides of the tapered duct (4) is equipped with motion sensor channels (5) adjusted to the angles according to the anus. The waste coming from the upper portion end part (3) contacting the anus passes through the tapered duct (4). The inner surface is made of a very slippery smooth material to minimize waste contact to the inner surface of the tapered duct (4).

Ring (6)

The ring (6) is secured between the tapered duct (4) and the top cover (9) of the slide (10). The ring (6) is provided with a plurality of holes (8) with different inclinations according to multi-hole ejector, the inner wall of the tapered duct (4) and the anus. Hygienic materials and clean water can be sprayed from said holes to ensure the necessary cleaning in areas contaminated with the waste. After this process, hot air blowing process is carried out at the appropriate pressure, thus providing full hygienic cleaning in the anus area. The ring (6) ensures the water and air inlet by the water-air inlet opening (7).

Slide (10)

The slide or lapel (10) is provided with a two-stage electromagnetic coil mechanism (12), which can give rapid mechanical response in order to perform the warning of motion sensors very quickly when the waste leaves the patient's body. In addition, the electro-magnetic coil mechanism (12) ensures that the slide or lapel mechanism, which is the most critical mechanism of the functional underwear, is opened quickly under any circumstances in the event of a failure. Since the path of the wastes will be closed otherwise, the patient will face a very difficult situation. Therefore, the system is supported with a two-stage electromagnetic coil mechanism (12) in order to eliminate the possible malfunctions.

Inclined Waste Pump (13)

The body of the inclined waste pump (13) mounted in functional underwear device (1) is designed as inclined. This is for providing fluidity to wastes and ensure the descend of the wastes into the storage with the help of gravity by spraying the water of the water pump in the ejector (20) portion or the chemical proving on the surfaces with a inclined waste pump (13) having a suitable pressure in case of failure of the electromechanical motor (14) which rotates the borer inside the pump body.

Waste Storage (22)

In the previous patent application for the physically disabled patient support unit (TR-2009/01453), the waste storage was located in the lower portion of the unit. In the invention, the waste storage (22) is placed in the lower portion of the seat (21), which is the seating portion of the unit. Thus, even if the electromechanical waste transfer pump (30) fails, the waste is made fluid with the effect of gravity due to the level difference and with the help of water spraying ejectors mounted on the pipe elbows, thus transferring the wastes to the waste transfer station, to the waste storage (22) even without the help of the motor, and from the storage outlet pipe (25), through the pipe (24) mounted inside the moving step (23) of the patient sitting in the unit, to the station.

Moving Step (23)

In the previous patent application (TR-2009/01453) of the physically disabled patient support unit, the waste transfer mechanism was driven by the electromechanical mechanism in the lower part of the unit and clamped front side of the waste transfer station on the lower portion of the front side of the cabin portion of the unit. In this case, when the discharge of wastes is completed, the drippings in the pipe where the wastes go through while leaving the station causes a risky contamination in the area where the unit and the station is located. Therefore, in order to prevent this drawback, the properties of the unit is utilized to transfer the waste to the station with the level difference.

In the invention, the moving step (23) used as a step by the patient as well as allowing the patient perform gymnastics can move up and down, and thus with the help of the pipe (24) inside the moving step (23) the wastes are transferred to the waste transfer station from above. In this case, the electromechanical valve (31) is closed and the waste passage is stopped before the fluid in the waste pipe leaves the station with the support of the ejectors and the effect of gravity, even if the electromechanical waste transfer pump (30) fails. However, the infiltration time is extended slightly and infiltration toward the end portion of the pipe (24) outlet of the moving step (23) is ensured. As a result, dripping is prevented and the wastes will be transferred to the waste transfer station easily in a hygienic manner.

The moving step (23) transforms the unit into a chair with the warning of the sensors from the moment the wastes of the patient leaves the body, lifts the feet up and brings the patient to a squatting position, thus ensuring an easier discharge of the patient's waste.

Waste Transfer Station (35)

In the previous patent application for the physically disabled patient support unit (TR-2009/01453), the transfer of the waste happened in the front side if the station. In the invention, the portion (32) on the upper portion of the waste transfer station (35) and the fresh water inlet (33) are coupled to the DC power socket (34), which will supply the DC power from the unit to the station (to the solenoid washing the station systems and to the city mains water solenoid connected to the station). Coupling with the pipe (24) inside the moving step (23), during the transfer of the wastes to the station with the gravity effect and the support of the ejectors and during the separation of the unit due to coupling in the station, the infiltration time before the waste pipe leaves the station is extended slightly and infiltration from the pipe (24) to the portion (32) occurs. As a result of these processes, hygienic environment is provided by preventing the risk of dripping in the environment and places where the unit will be located.

Seat Belt (36) with Apparatus (37)

In the previous patent application of the physically disabled patient support unit (TR-2009/01453), the seat belts were designed to secure the patient to the unit. In the invention, a seat belt (36) with a new apparatus is provided. Patients with severe cases or overweight patients may need the examination of their backs. This can be performed with the help of the nurses. Additionally, in cases requiring minimum contact with the patient's body such as severe traumatic cases, burns etc., minimizing the pressure effect is very important. Therefore, the seat belt (36) with apparatus makes it possible for the patient to hang vertically at the desired level at different vertical inclinations. This facilitates the physician or facilitates the transfer of the patient to another vehicle or device, as well as acting as support by improving the patient's comfort.

The seat belt (36) with apparatus (37) is stored in the enclosure (26) mounted on the top portion of the top of the unit. The two ends of the seat belt (36) with apparatus are fixed to the electromechanical mechanism (27) mounted inside the lower portion of the enclosure (26) at the top portion of the unit. The forward and backward motion of the seat belt (36) with apparatus is driven by the electromechanical mechanism (27).

The two sides of the seat belt (36) with apparatus (37) are mounted on the lower portion inside the enclosure (26), fixed by the electromechanical mechanism (27), the belts in the first lower stage (38) of the apparatus (37) covering the patient's chest from both shoulders of the patient on the head side passes through the inner portions of the channels and coupled to the opposite sides (42) fixed to the construction of the back of the unit hidden under the bed on the portion where the side wings of the unit bend. In this case, the patient's chest and the belts (36) are fixed to the multi-stage apparatus (37) which covers the patient's chest.

Multi-Stage Apparatus (37)

The multi-stage apparatus (37) comprises a plurality of stages. It is large enough to cover the abdomen and chest of the patient to the appropriate distance to the patient's throat. The first lower stage (38) contacting the patient's chest is covered with material that will absorb the pressure of the patient, such as a soft viscose sponge or an air-inflatable pad on the surface contacting the patient's chest. The pressure is absorbed and the patient's comfort is not disturbed while providing forward inclination when the patient is in the upright position. The multi-stage apparatus (37) consists of four stages. The first stage is the first lower stage (38) which contacts patient's chest, and the second stage (39) is the outer housing cover. When the outer housing cover is opened in a V-shaped direction, the third stage (40) is formed in order to serve as a portable table. This stage creates a flat area to meet the needs of the patient such as food etc. When the third stage (40) cover is removed, the fourth stage (41) is formed, which contains a tablet computer embedded in the middle of the fourth stage (41), and a joystick on the right side of the tablet computer so that the patient can manage the unit. The patient will be able to control the unit so that it can be controlled easily.

Bed (46)

The movement of the bed section on the system of the unit in all the desired directions is provided by the pistons with electromechanical mechanism mounted on four corners forming the skeleton of the unit, which can move independently of each other. Both the head and foot sides can be raised or lowered, tilted to the right or left, can become a seat, or make the patient standing in a fully upright position. In addition, both sides can move evenly up and down in parallel. All these properties of the bed facilitate the transfer of the patient to different vehicles or different devices, and the examination of the various body parts of the patient. Due to all these properties of the bed (46), the patient's body will move, preventing the formation of bed sores.

The bed side wings (29) located on the head side of the bed can be opened and closed by the electromechanical wings mechanism (28), which enables the bed side wings to open and close independently of each other. This facilitates the replacement of the bed.

Side Wings (29)

The unit is provided with a folding mechanism (47) ensuring the mechanical relation of the side wings (29) located on both sides of the unit and composed of three sections and ensuring the side wings to move together.

The side wings (29) located on both sides of the unit are composed of three sections, which are, independently of each other, back stage side wings, seat stage side wings, and leg stage side wings. The back stage side wings (29) at the shoulder level of the patient are driven by electromechanical wings mechanisms (28). In order to provide a mechanical relationship between the other two stages, the seat and the leg stage side wings (29), folding mechanisms (47) are mounted in the interior of the side moving sections. By means of the folding mechanisms (47), the distance between the stages of the side wings (29) is moved closer and away while the unit is moved to seat-bed and vertical positions. By means of the folding mechanisms (47), the gap between the seat and the leg stage side wings is prevented. Therefore, both the formation of a gap in this region is prevented and the seat and leg stage side wings (29) are moved together in a strong manner.

In the same way, there are folding mechanisms (47) between the back stage side wings (29) and the seat stage side wings (29). The folding mechanisms (47) mounted on the inside of the moving parts of the side wings (29) are fixed to the back stage side wings (29) on the one end and on the seat stage side wings (29) on the other end in such way to cover the outer surface. Said folding mechanisms (47) are opened and seated when the unit turns into a bed, closing the gap formed between the seat section and the back section side wings (29). Thus, the casing of the contact surface of the bed or the sheet-like materials are prevented from tangling jamming in the side wings. The folding mechanisms (47) which are hidden inside are prevented from contacting the bed or the sheet during the mechanical movement. Likewise, one end of the side wings (29) is fixed to the leg portion while the other end is fixed to the seat stage side wing (29).

On the head side of the unit, there are connecting clamps (48) mounted on both sides and back stage side wings (29) and connecting clamps (49) mounted on both sides of the head side. These connecting clamps (48, 49) have an elastic casing shell covering the gap formed during the opening and closing of the side wings (29). Thus, the materials such as quilts or bed sheets etc. are preventing from entering this section.

Cover Attached to Seat Belt

Along with the models covering the chest area of the seat belt (36) with apparatus, a cover attached to the seat belt is designed for the patients who cannot control their bodies such as paralyzed-bedridden patients. The cover attached to the seat belt extends across the entire length of the unit to the ankle to cover the entire body of the patient. Paralyzed-bedridden patients cannot control the bending of their knees. Therefore, it is necessary to prevent the knees bending during the forward suspension of the patient and to ensure that the patient's body stays upright. Therefore, the inner surface of this cover is designed to have necessary strength to prevent the patient's knees from bending during the forward suspension of the patient and the undesired physical behavior of the patient, the inner surface of this cover in contact with the patient's body is covered with soft material.

PARTS OF THE SYSTEM

Figure 1:
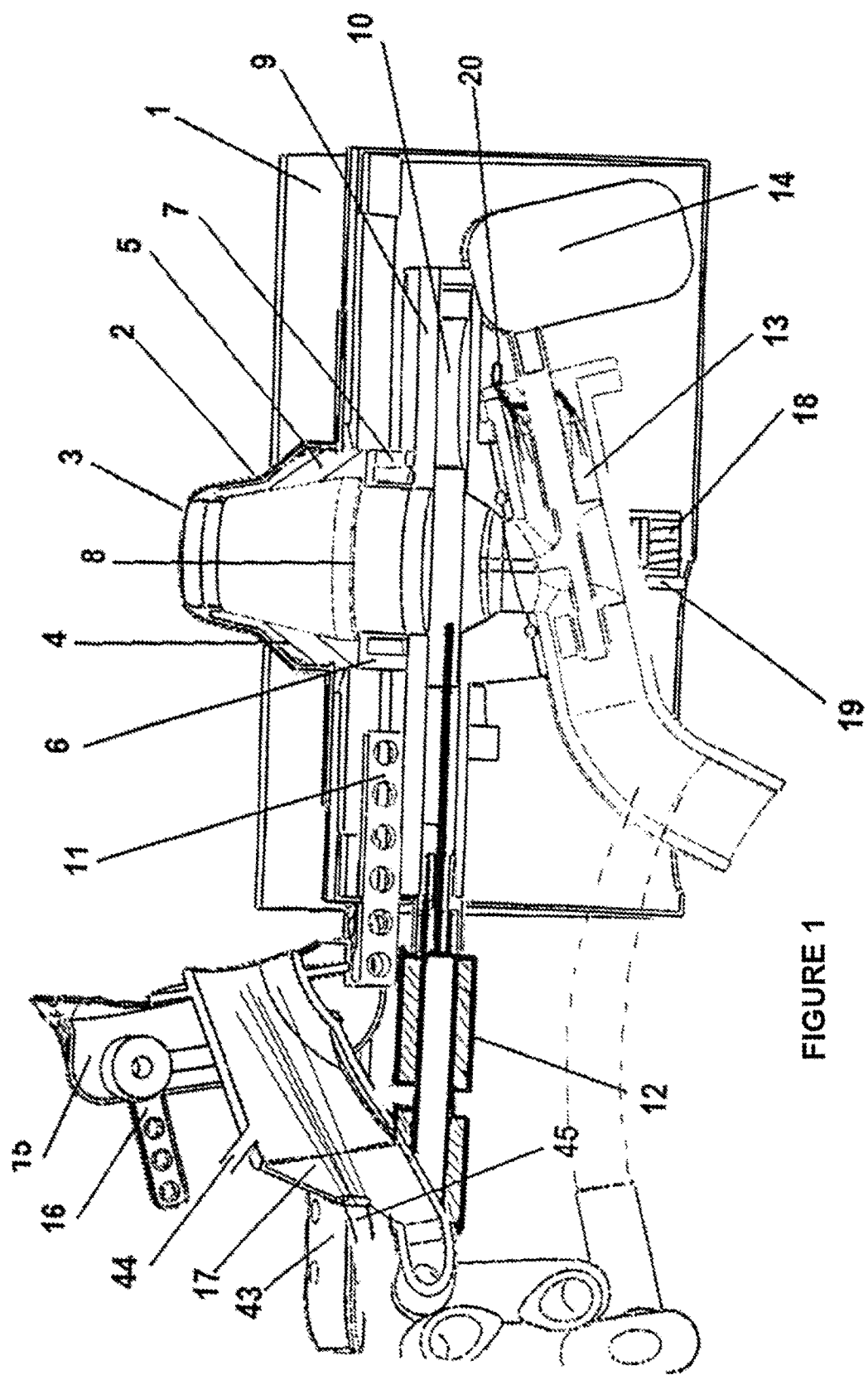
FIG. 1: Side sectional view of functional underwear device.
Figure 2:
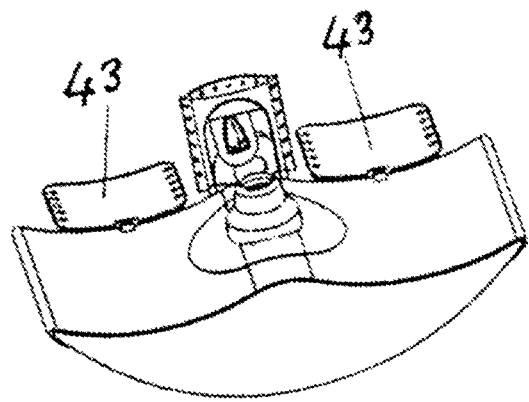
FIG. 2: Back view of functional underwear device.
Figure 3:
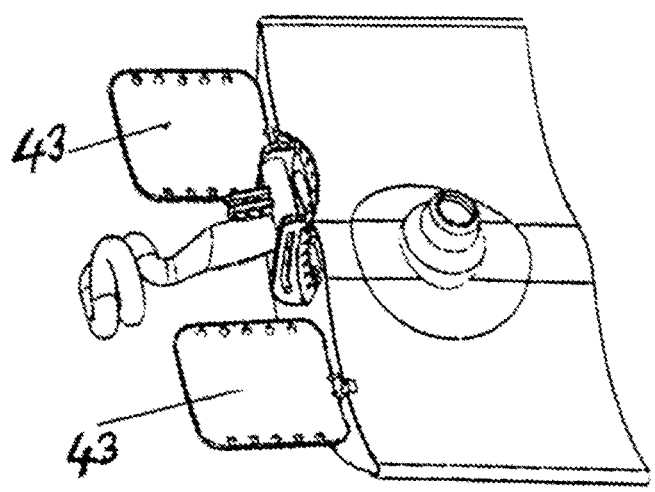
FIG. 3: Top view of functional underwear device.
Figure 4:
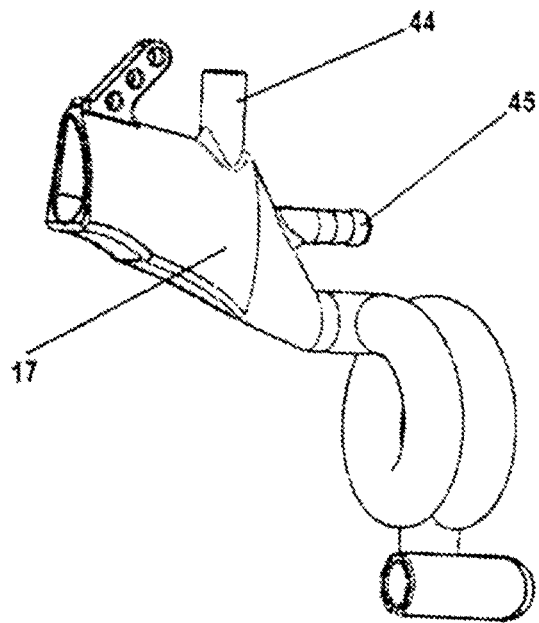
FIG. 4: General view of urine removal apparatus in functional underwear device for women.
Figure 5:
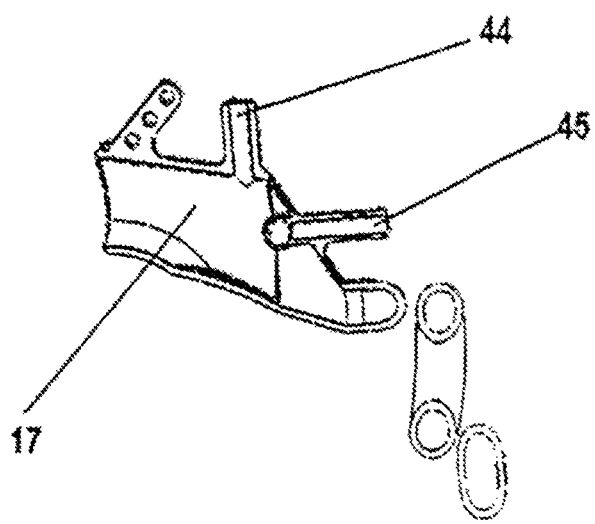
FIG. 5: Section view of urine removal apparatus in functional underwear device for women.
Figure 6:
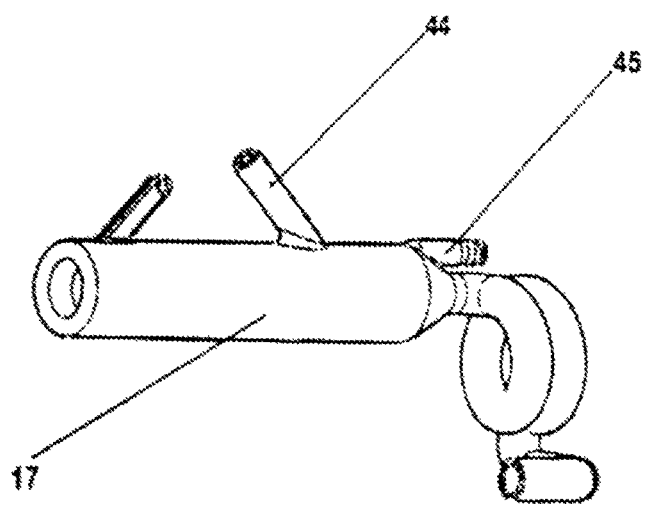
FIG. 6: General view of urine removal apparatus in functional underwear device for men.
Figure 7:
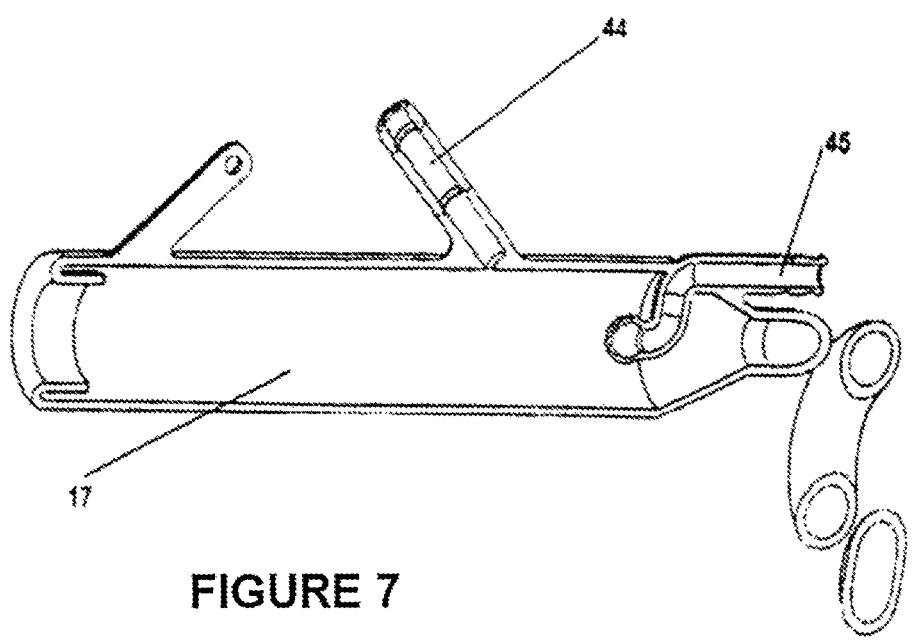
FIG. 7: Section view of urine removal apparatus in functional underwear device for men.
Figure 8:
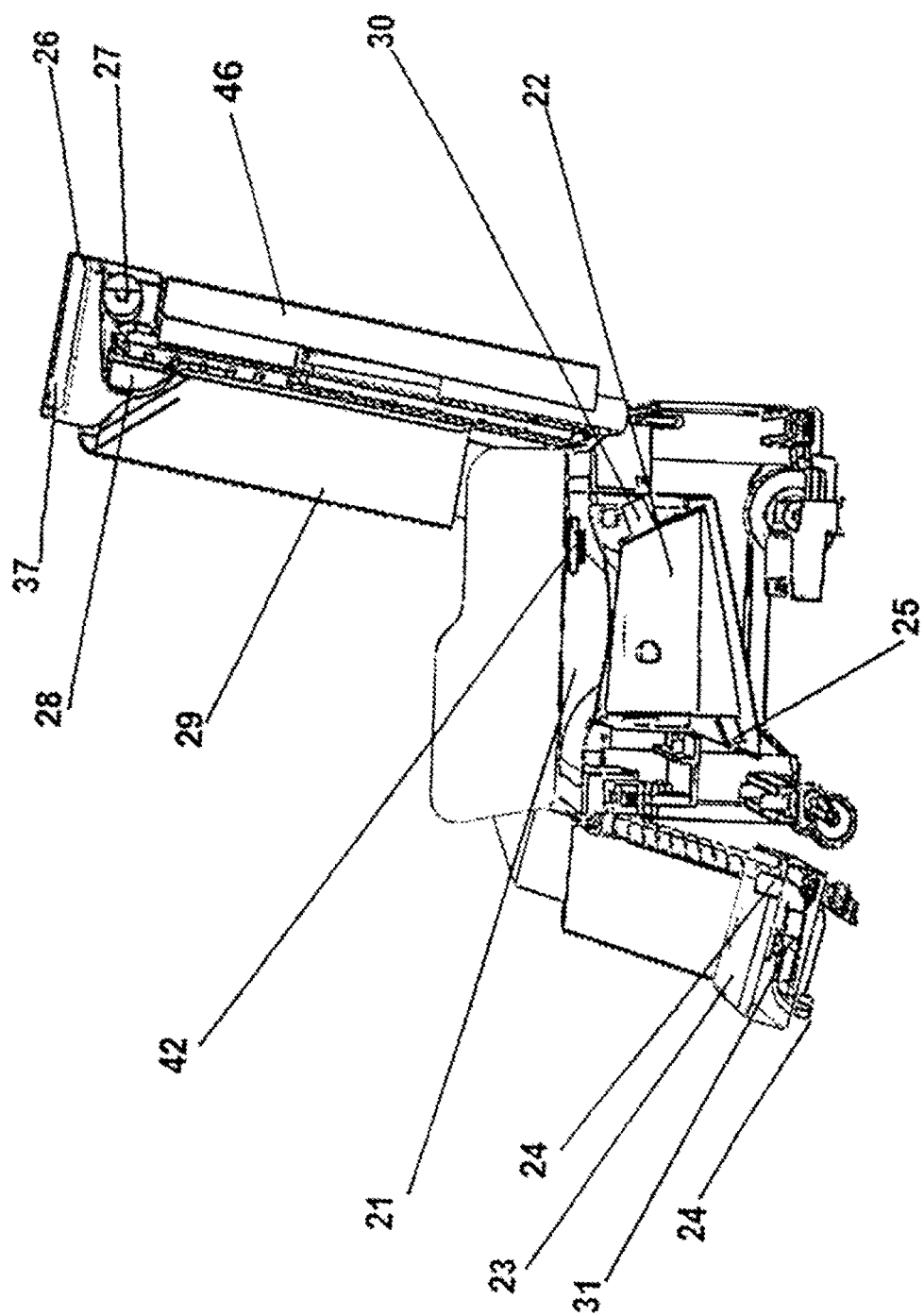
FIG. 8: Side sectional view of the seat state of the physically disabled patient support unit.
Figure 9:
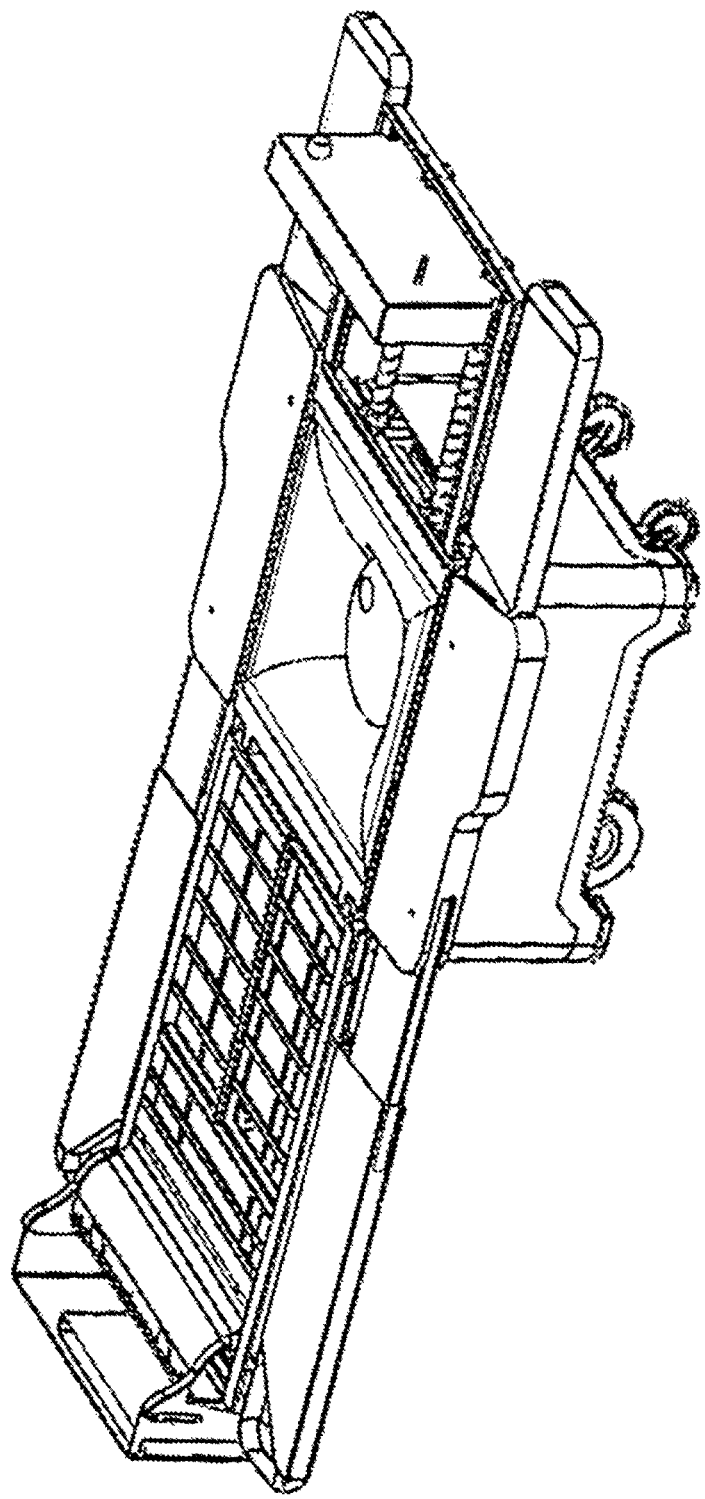
FIG. 9: General view of the physically disabled patient support unit on horizontal position with lateral sides open.
Figure 10:
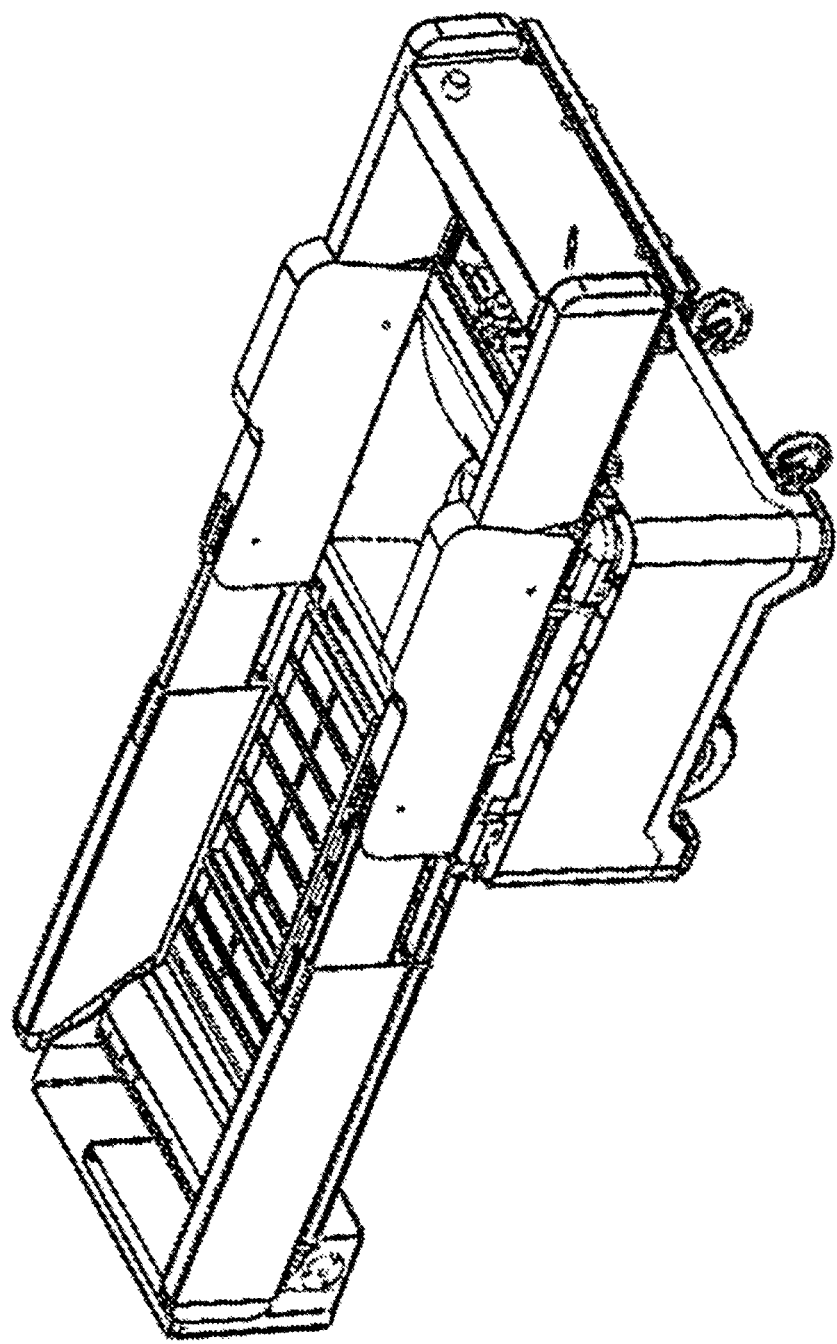
FIG. 10: General view of the physically disabled patient support unit on horizontal position with lateral sides closed.
Figure 11:
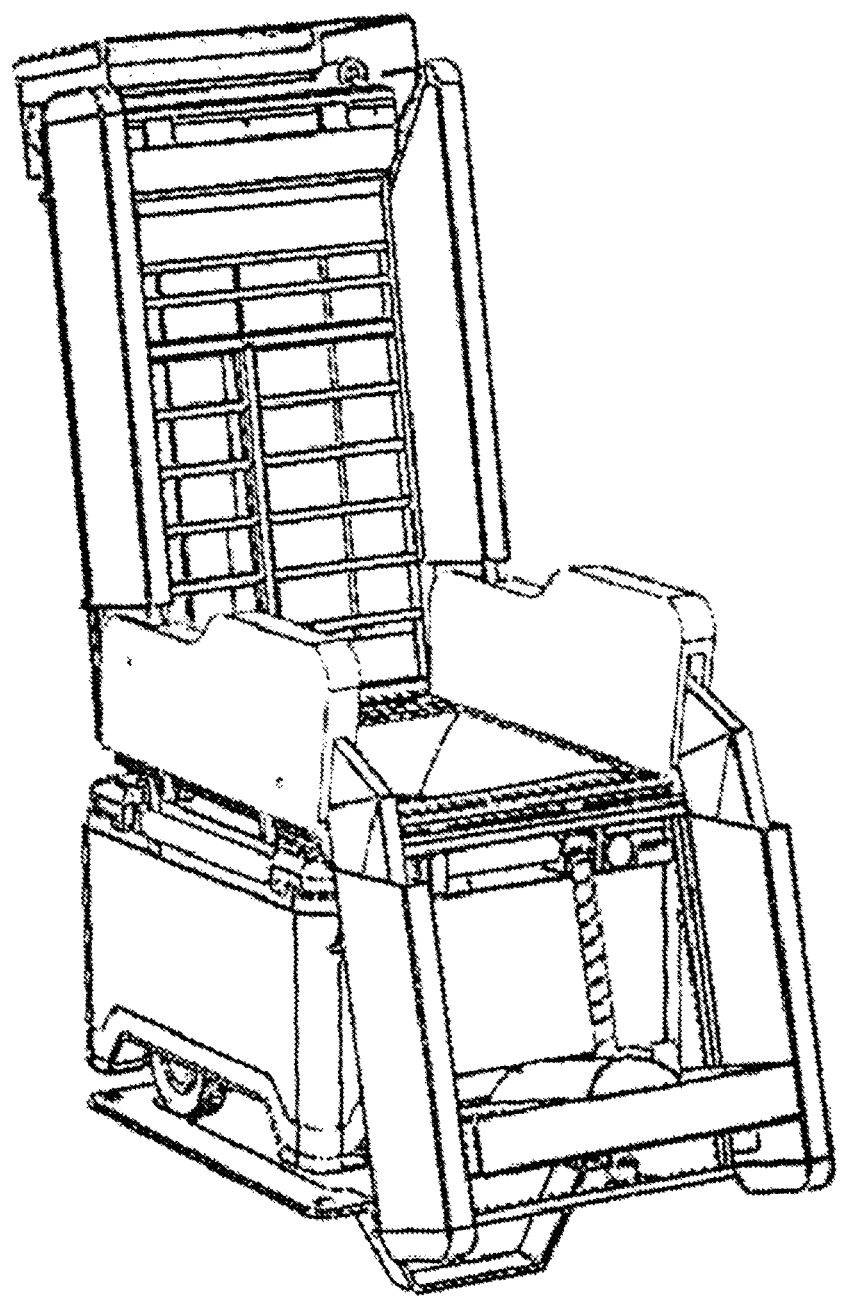
FIG. 11: General view of seat state of the physically disabled patient support unit.
Figure 12:
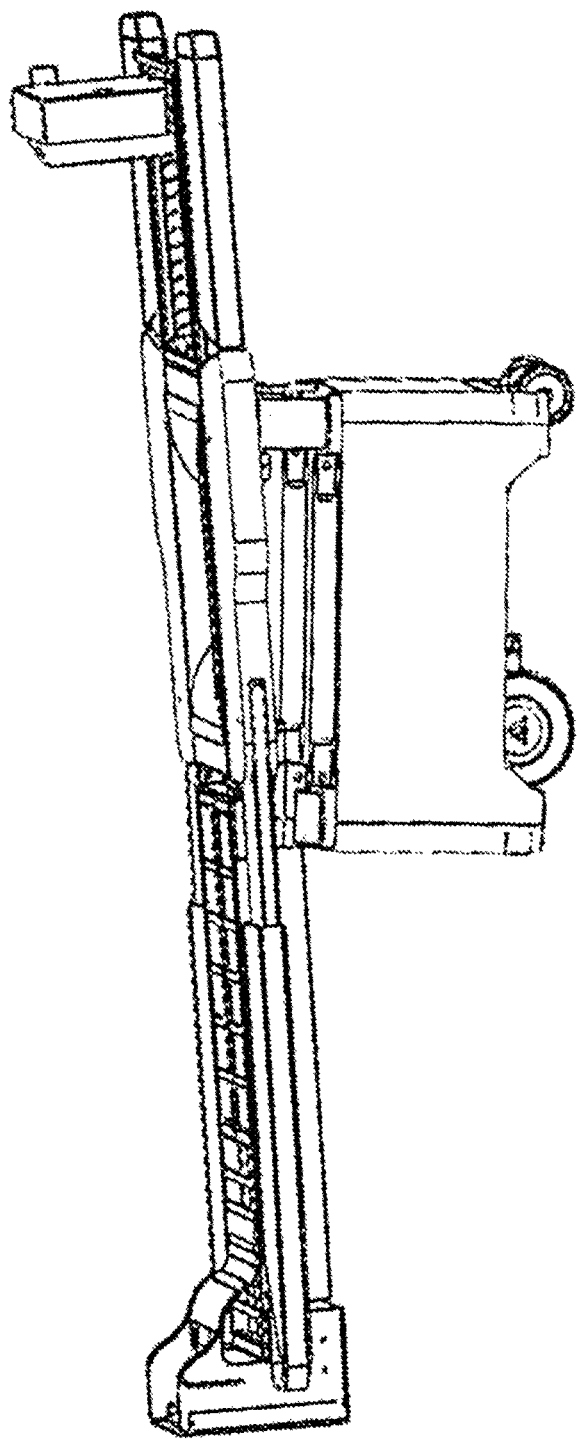
FIG. 12: General view of the physically disabled patient support unit on horizontal position with feet side elevated.
Figure 13:
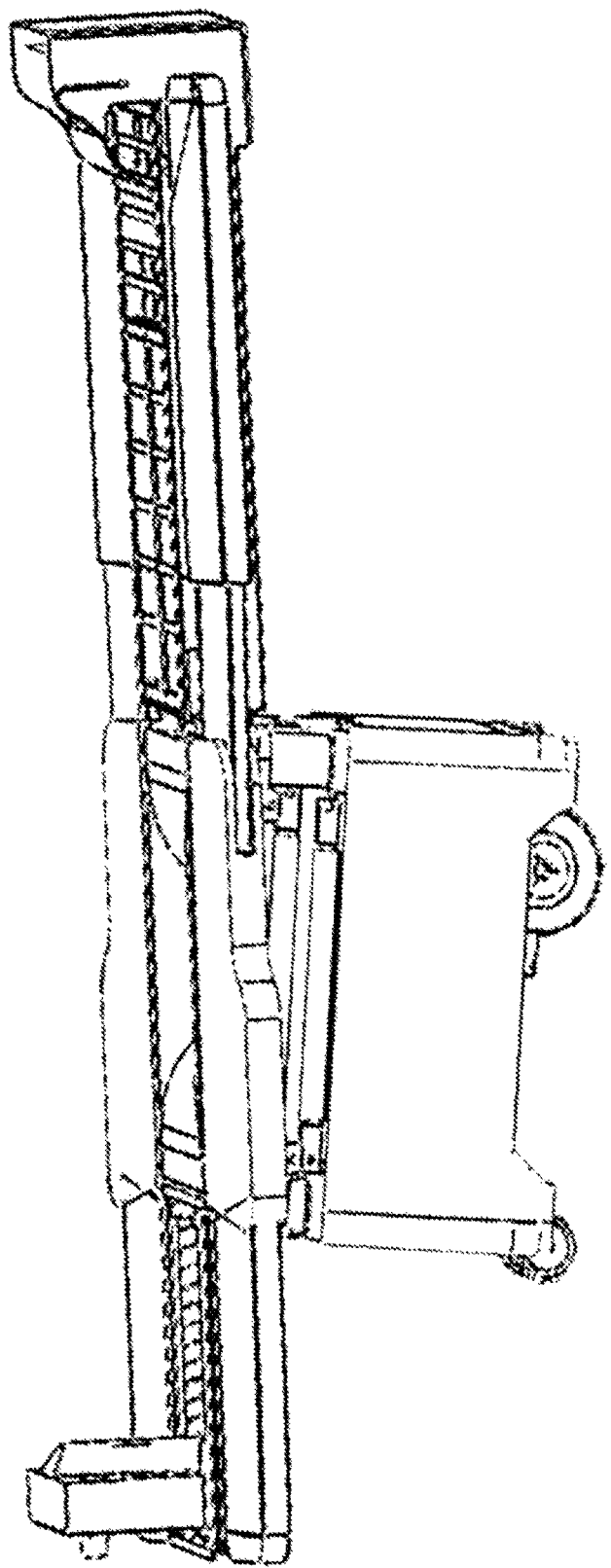
FIG. 13: General view of the physically disabled patient support unit on horizontal position with head side elevated.
Figure 14:
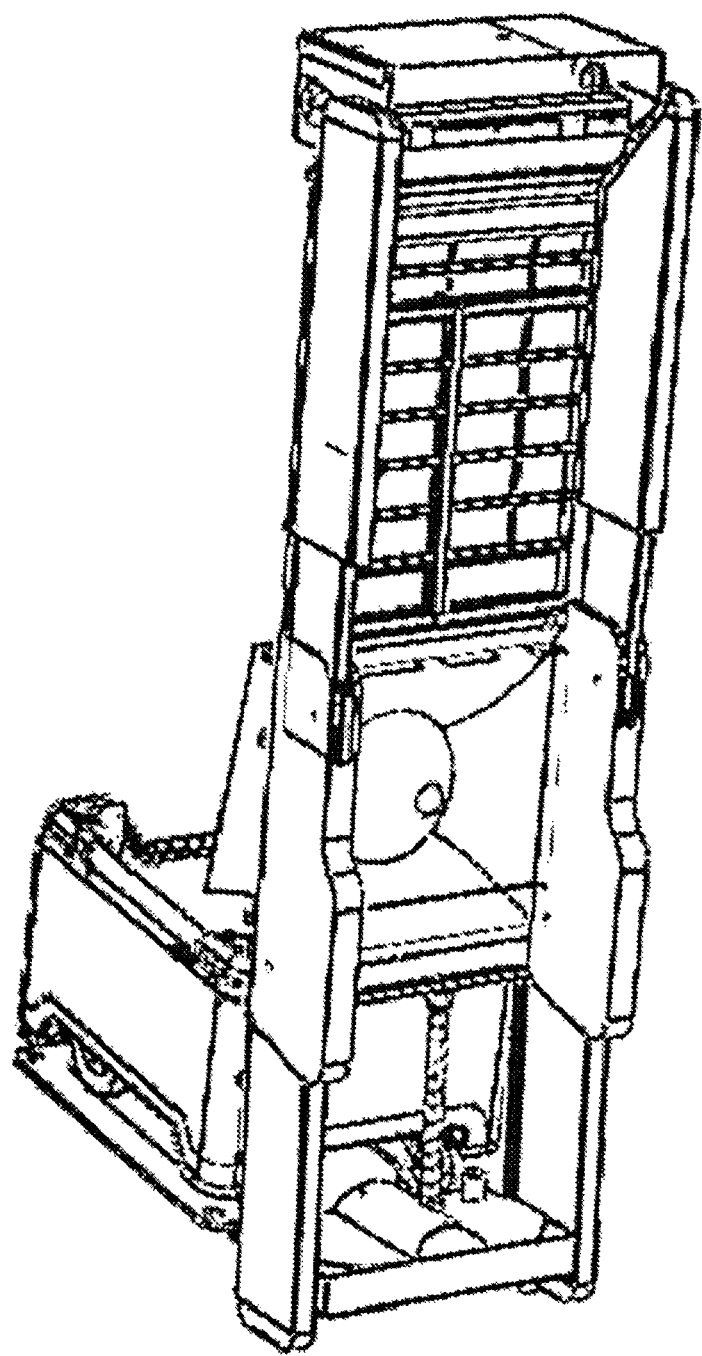
FIG. 14: Front view of the physically disabled patient support unit while fully upright.
Figure 15:
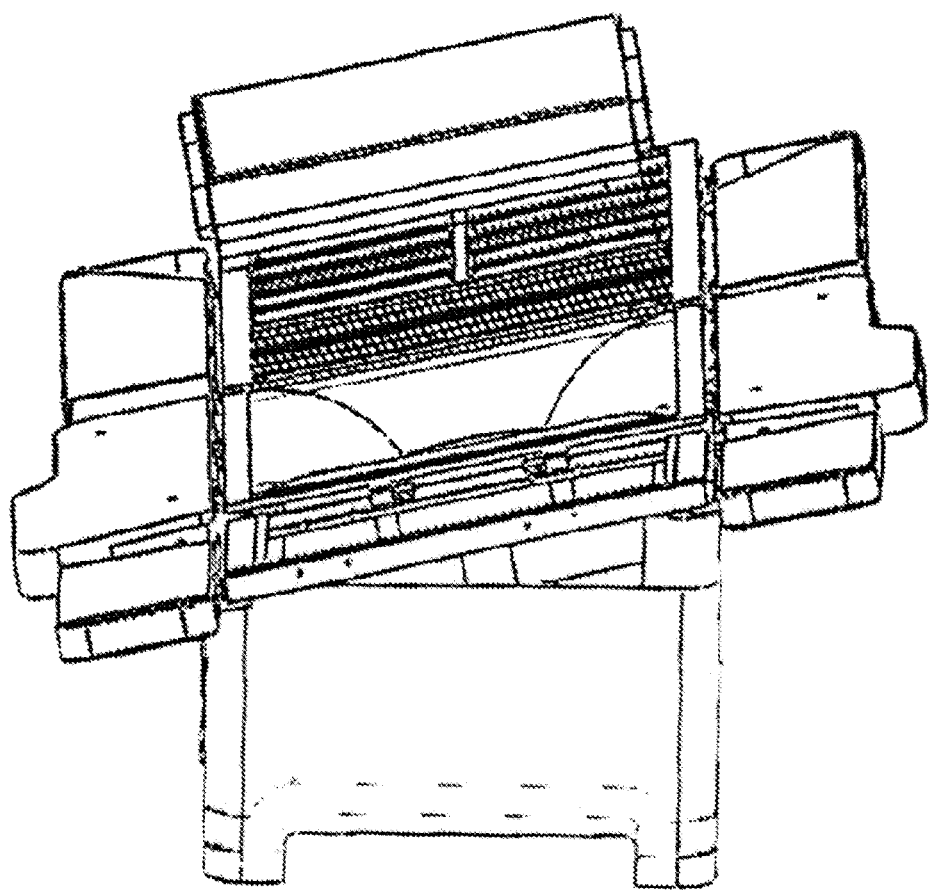
FIG. 15: Feet side view of the physically disabled patient support unit on horizontal and left tilted position.
Figure 16:
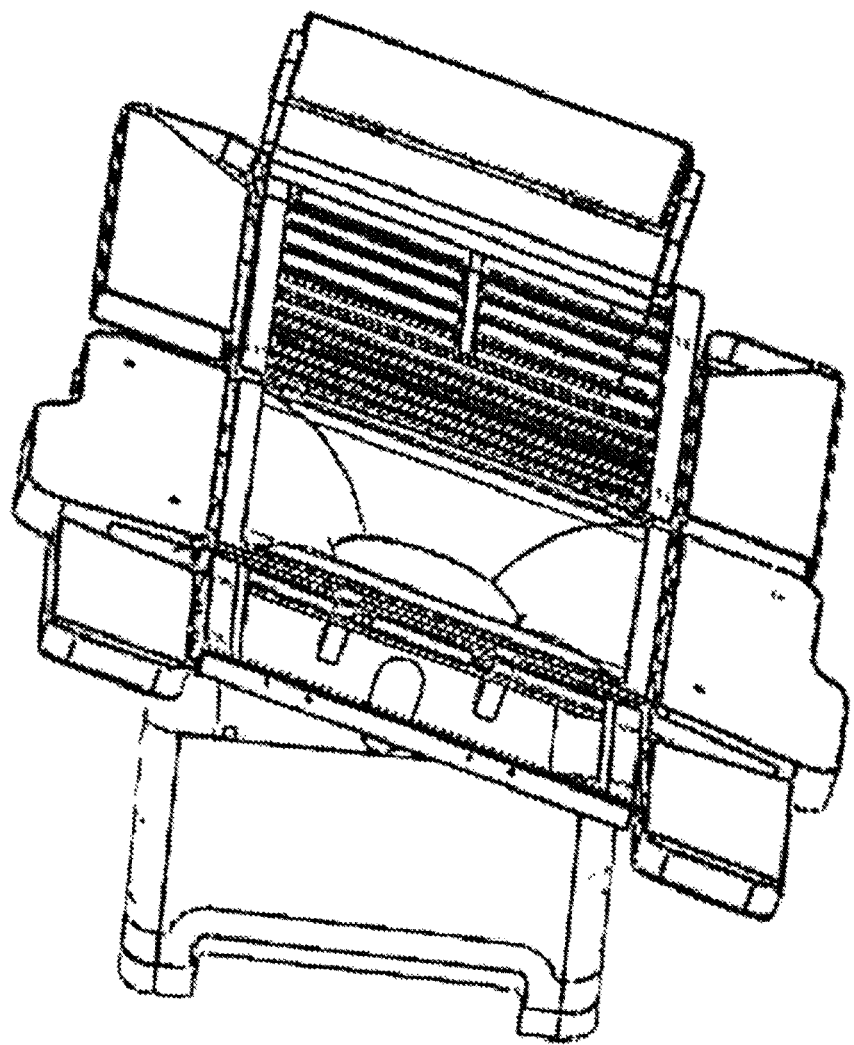
FIG. 16: Feet side view of the physically disabled patient support unit on horizontal and right tilted position.
Figure 17:
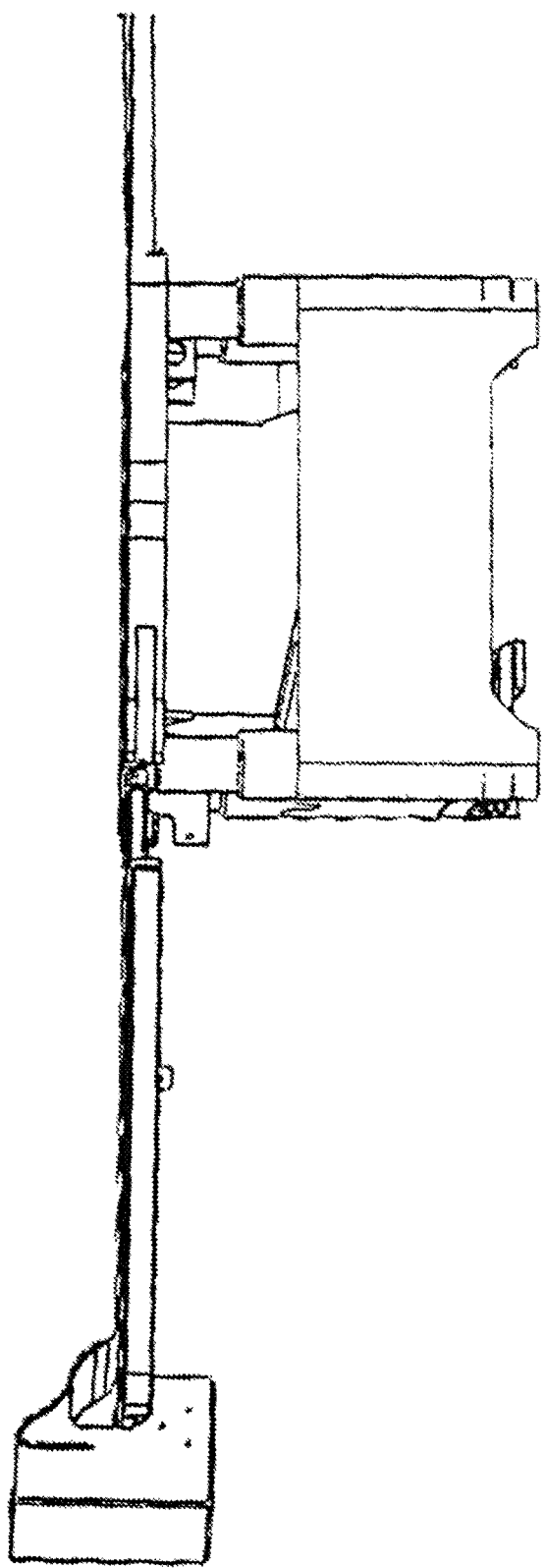
FIG. 17: Side view of the physically disabled patient support unit on horizontal position with both sides elevated equally.
Figure 18:
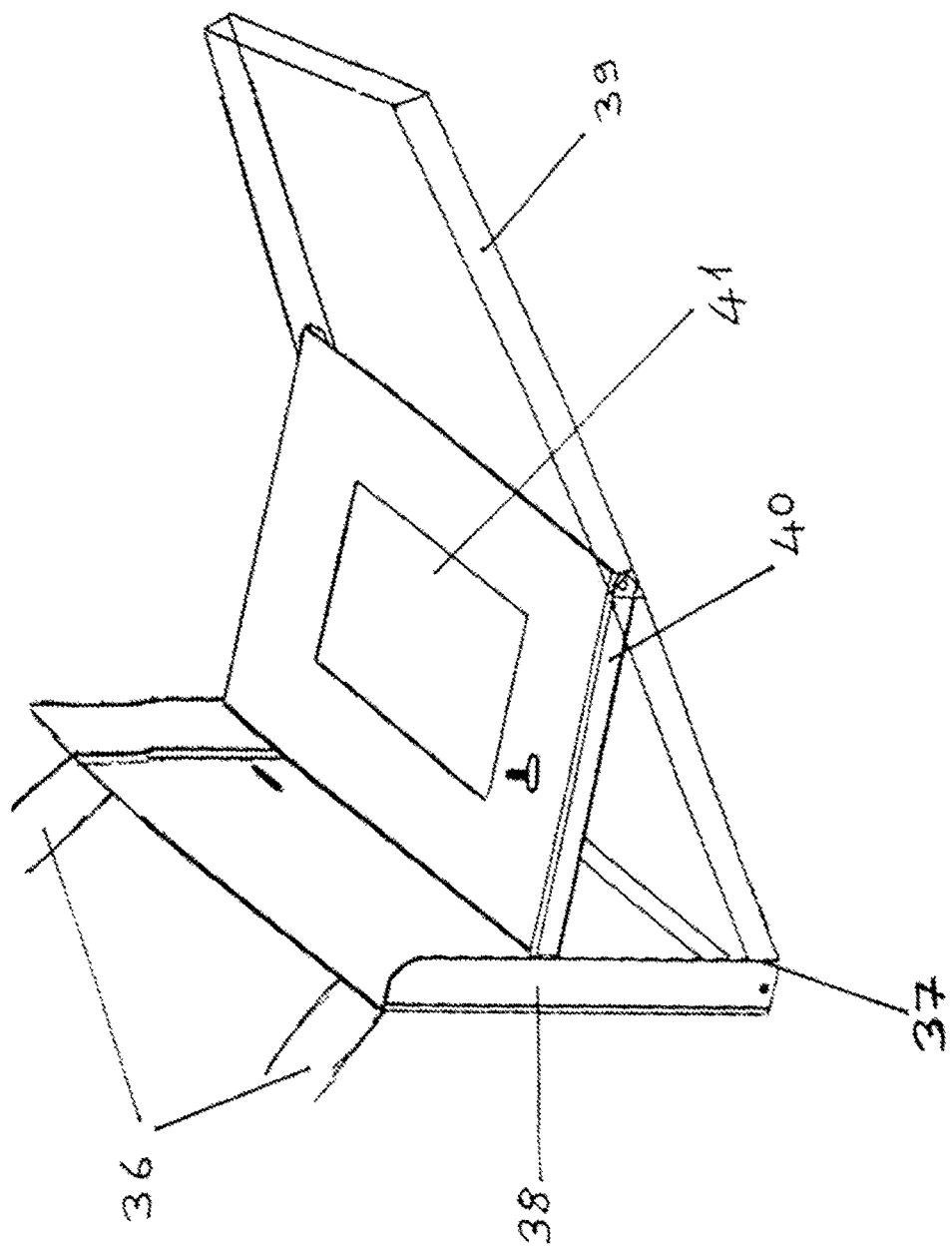
FIG. 18: General view of multi-staged apparatus and seat belt with apparatus together.
Figure 19:
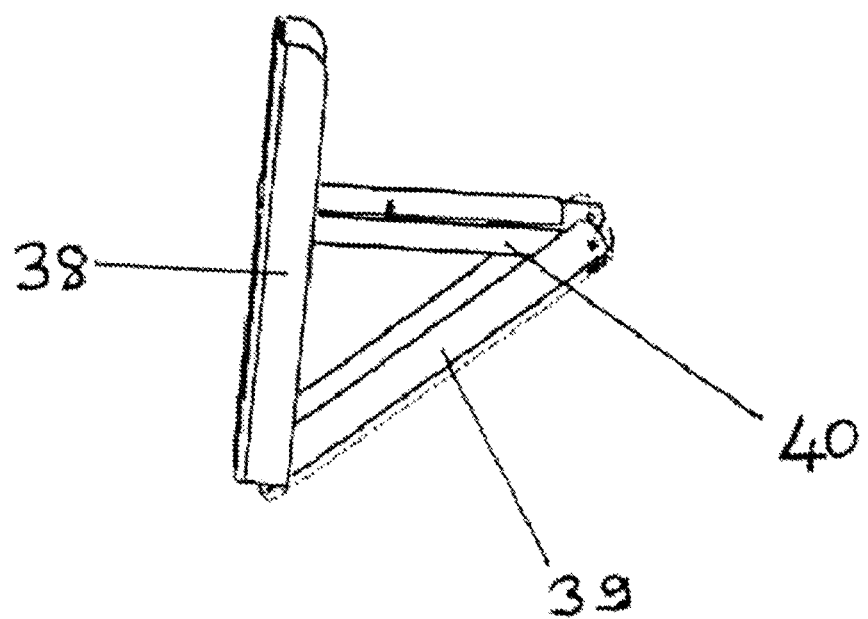
FIG. 19: Side view of seat belt with apparatus.
Figure 20:
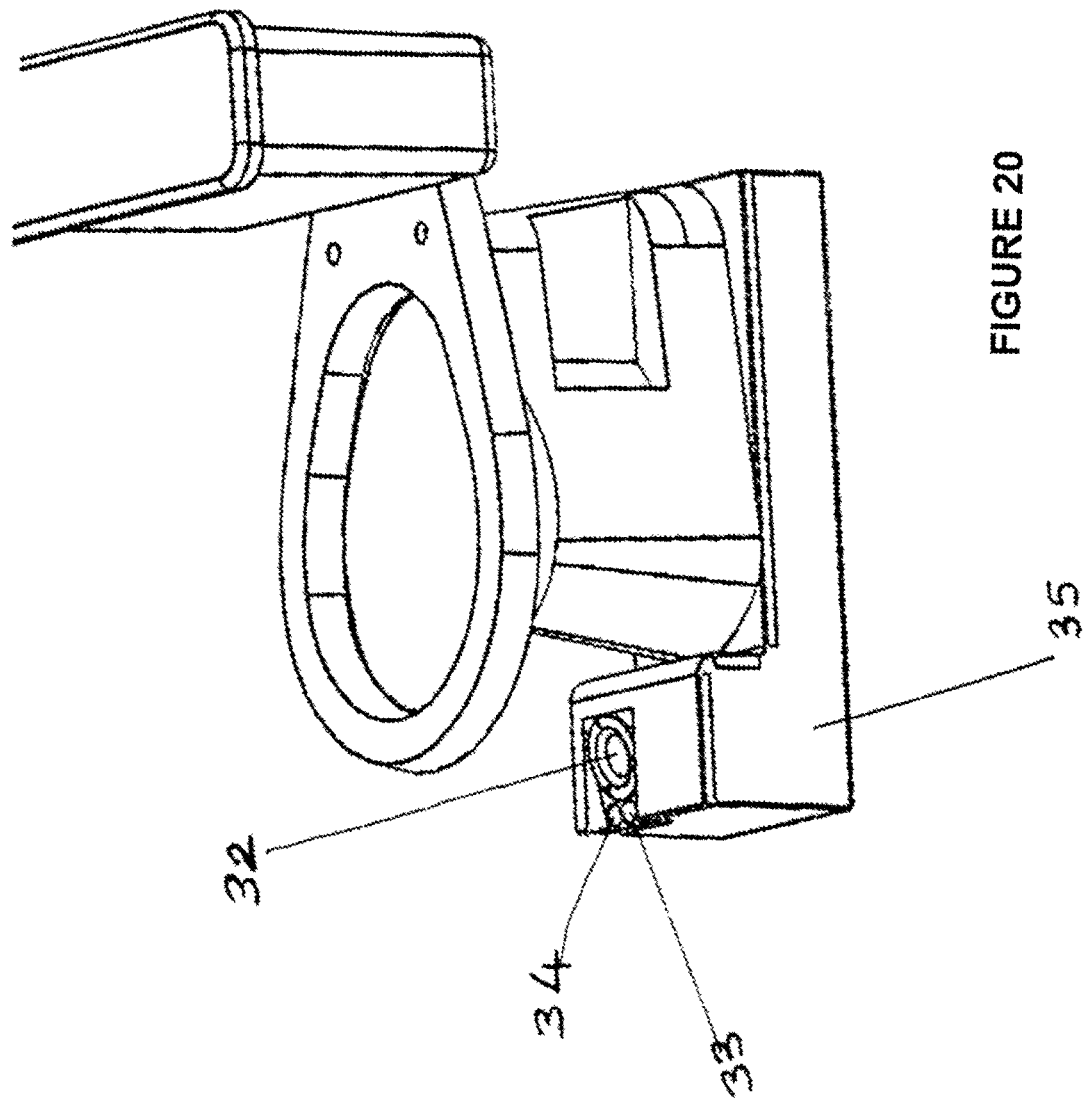
FIG. 20: General view of waste transfer station.
Figure 21:
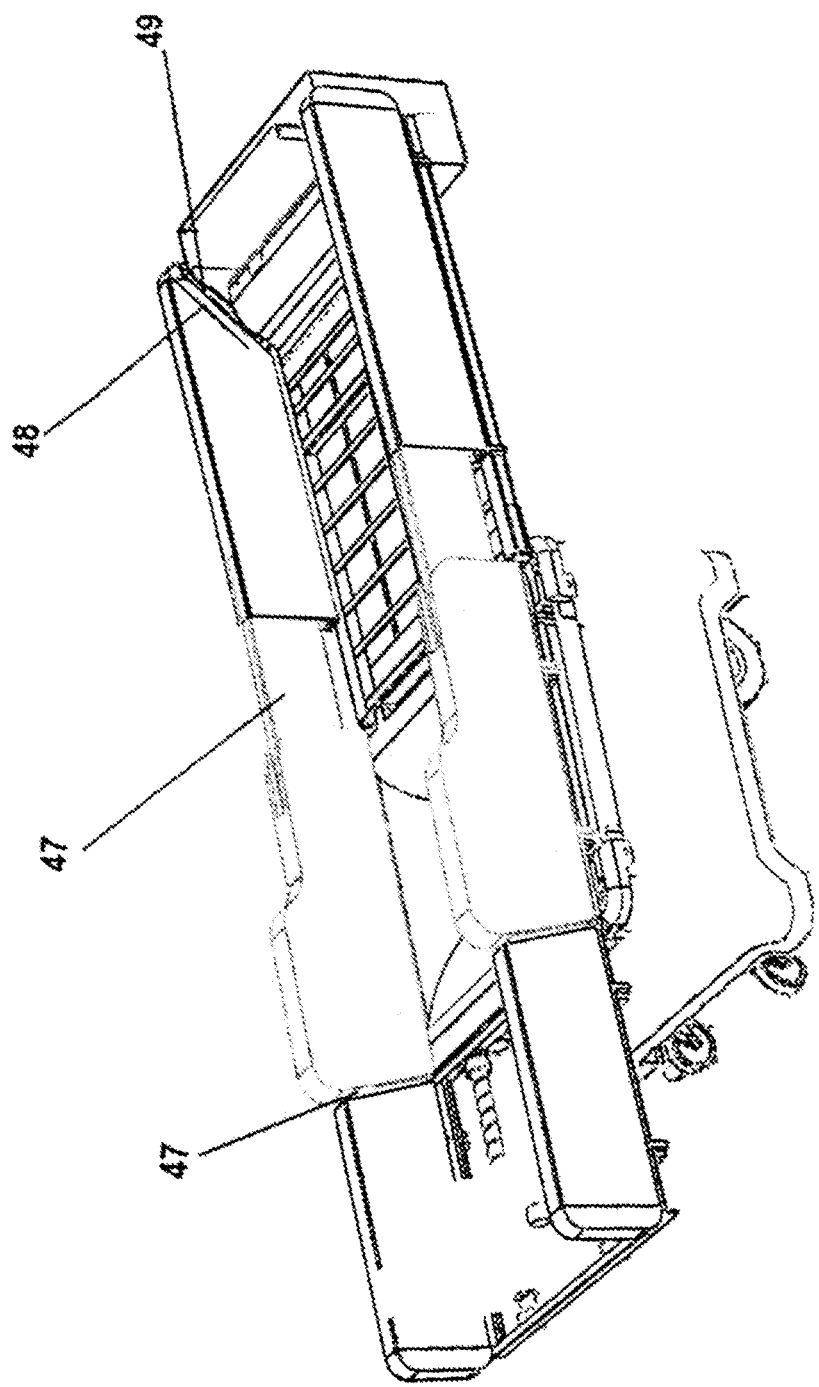
FIG. 21: Open view of the folding mechanism (47) between the side wings (29) of the back stage and the seat side wings (29).
Figure 22:
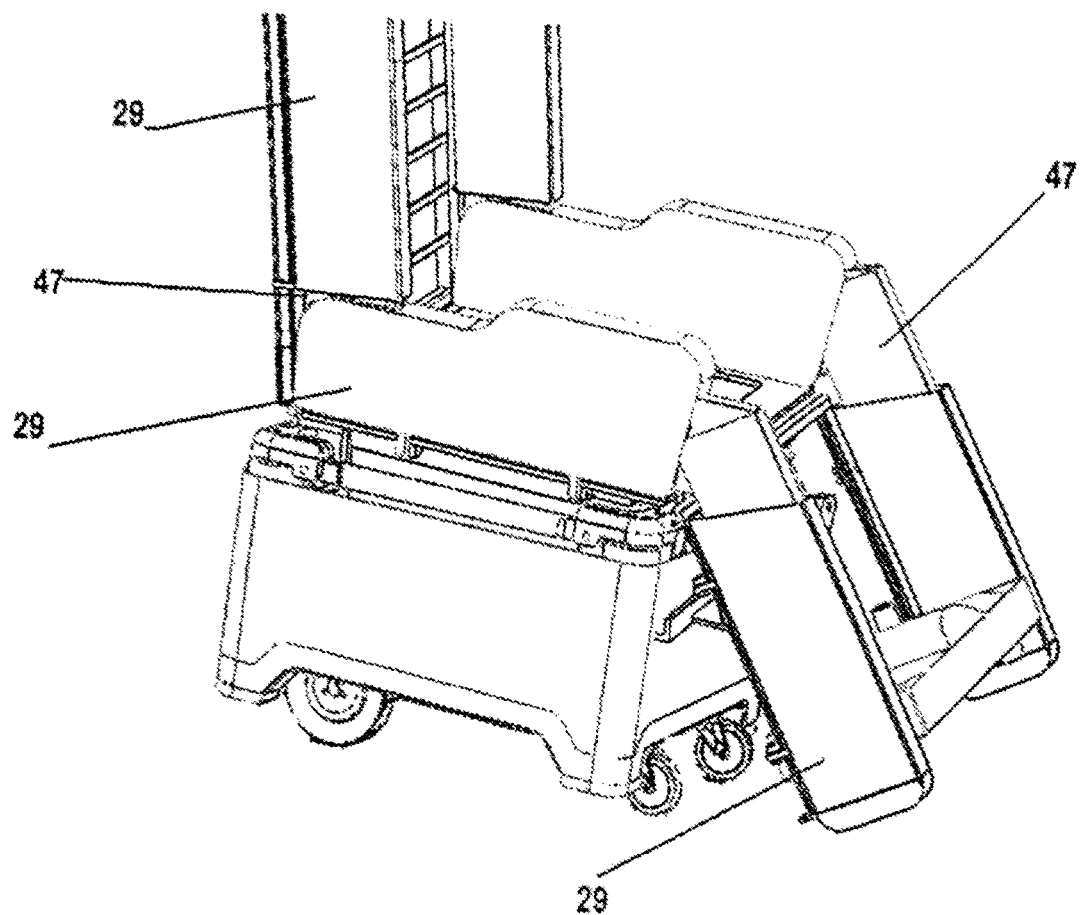
FIG. 22: Open view of the folding mechanism (47) between the seat side wings (29) and the leg stage side wings (29).

1. Functional underwear device
2. Silicone casing shell
3. Upper portion end part
4. Tapered duct
5. Motion sensors channels
6. Ring
7. Water-air inlet opening
8. Holes 9. Top cover
10. Slide
11. Movable mechanism
12. Electromagnetic-coil mechanism
13. Inclined waste pump
14. Electromechanical motor
15. Chassis
16. Mechanism
17. Urine removal apparatus
18. Electromagnetic coil
19. Railed mechanism
20. Ejector
21. Seat part
22. Waste storage
23. Moving step
24. Pipe
25. Storage outlet pipe
26. Enclosure
27. Electromechanical mechanism
28. Wings mechanism
29. Side wings
30. Electromechanical waste transfer pump
31. Electromechanical valve
32. Portion
33. Fresh water inlet
34. DC power socket
35. Waste transfer station
36. Seat belt
37. apparatus
38. First lower Stage
39. Second Stage
40. Third Stage
41. Fourth Stage
42. Opposite sides
43. Palletes
44. Motion sensor
45. Urine area ejector
46. Bed
47. Folding mechanism
48. Connection clamp
49. Connection clamp

What is claimed is:

1. A support unit for a physically disabled patient support unit comprising: a functional underwear device comprising pallets configured to be fixed to the patient after centering the anus of the patient over the device after separating the buttocks to both sides, the pallets configured to support both calves of the patient and are configured to move independently; a silicone shell casing on the device, an upper portion end part of the silicone shell casing configured to contact an area around the anus when an inclined waste pump supported by a rail mechanism located on a lower portion of the support device is lifted, the inclined waste pump being mounted inside the functional underwear device and configured to provide fluidity to wastes and ensure the descent of the wastes into a waste storage positioned below a seat portion of the support unit; an electromechanical motor which rotates a borer inside the inclined waste pump; an electromagnetic coil boated inside the rail mechanism configured to ensure a flow of the waste into the inclined waste pump in a controlled manner by rapidly controlling an opening of a slide, the slide being configured to be pulled open by the electromagnetic coil mechanism when activated by a warning of motion sensors when the motion sensors detect waste of the patient, the slide, when closed, being configured to provides a hygienic environment by closing off relationship between the patient and the waste storage; a urine removal apparatus attached to a chassis of the device and configured to be located between the legs of the patient, the urine removal apparatus containing a motion sensor and a urine area ejector, the urine area ejector configured to enable a washing and cleaning of the urine removal apparatus with a hygienic material, a tapered duct with an upper portion mounted inside the functional underwear device beneath the silicone shell casing and whose lower portion is fixed to a top cover of the slide with a ring, two sides of the tapered duct being configured with motion sensor channels, the ring being provided with a plurality of holes with different inclinations according to an inner wall of the tapered duct, the plurality of holes being configured to allow a flow of water and air from a water-air inlet opening; a moving step connected to the chassis of the support unit that is configured to be used as a step by the patient; a pipe mounted inside the moving step and configured to transfer the waste from the waste pump to a waste transfer station.

2. The support unit according to claim 1 further comprising a storage outlet pipe connected to an end of the pipe mounted inside the moving step.

3. The support unit according to claim 1, wherein an inner surface of the tapered duct comprises a slippery smooth material.

4. The support unit according to claim 1, wherein a material of the silicone shell casing comprises a soft silicone, and the upper portion end part of the silicone shell casing that is configured to be in contact with the anus is thin and flexible.

5. The support unit according to claim 1, wherein surfaces of the pallets and surfaces of the functional underwear device that are configured to be in contact with the patient are coated with a material that comprises one or more of an antiperspirant, an anti-bacterial, a soft viscose sponge or an air-inflatable pad.

6. The support unit according to claim 1 wherein a distance between the upper portion end part of the silicone shell casing and the area around the anus is 4-5 mm when the inclined waste pump is in a lowered position, and wherein the upper portion end part of the silicone shell casing is configured to contact the area around the anus only when the motion sensors detect a discharge of waste from the patient and when the inclined waste pump is lifted.

7. The support unit according to claim 1, wherein a portion of the chassis of the support unit is configured to be positioned between the legs of the patient, a mechanism is mounted to this portion of the chassis and is configured to support the urine removal apparatus and enable a level adjustment of the urine removal apparatus towards an area where the urine exits.

8. The support unit according to claim 1, wherein the electromagnetic coil is a two-stage electromagnetic coil mechanism that is configured to provide a mechanical response to a detection of waste by the motion sensors.

* * * * *